United States Patent [19]

Griffiths et al.

[11] Patent Number: 5,728,108
[45] Date of Patent: Mar. 17, 1998

[54] ROTARY DRIVE MECHANISM FOR INSTRUMENT HANDLE

[75] Inventors: Jerry R. Griffiths, Pembroke; John Young, Jr., Truro, both of Mass.

[73] Assignee: TNCO, Inc., Whitman, Mass.

[21] Appl. No.: 821,103

[22] Filed: Mar. 20, 1997

[51] Int. Cl.$^6$ ..................................... A61B 17/04
[52] U.S. Cl. ...................... 606/139; 606/142; 606/143
[58] Field of Search ........................ 606/139, 144, 606/146, 148, 151, 205, 218

[56] References Cited

U.S. PATENT DOCUMENTS

| | | | |
|---|---|---|---|
| 4,448,193 | 5/1984 | Ivanov | 606/143 |
| 4,509,518 | 4/1985 | McGarry et al. | 606/143 |
| 4,576,166 | 3/1986 | Montgomery et al. | 606/143 |
| 4,598,711 | 7/1986 | Deniega | 606/143 |
| 5,049,152 | 9/1991 | Simon et al. | 606/142 |
| 5,573,541 | 11/1996 | Green et al. | 606/142 |

*Primary Examiner*—Gary Jackson
*Attorney, Agent, or Firm*—Timothy J. Shea, II; Stephen Y. Chow; Perkins,Smith&Cohen, LLP

[57] ABSTRACT

A handle and drive mechanism for providing a reciprocating rotary action of a driveshaft, first in one rotational direction and then reversing the rotational direction, suitable for suturing and other endoscopic operations.

13 Claims, 6 Drawing Sheets

ROTARY DRIVE MECHANISM FOR INSTRUMENT HANDLE

FIELD OF THE INVENTION

The present invention relates generally to medical instrumentation, specifically to articulating, handheld instruments used in surgery and microsurgery and for suturing and other reversing rotary action operations.

BACKGROUND

Endoscopic medical devices allowing extracorporeal manipulation of internally disposed surgical instruments are well known. These devices typically comprise an elongate driveshaft, having a cylindrical housing journalled thereon; the driveshaft and the housing together defining a distal end and a proximal end. A variety of medical instruments, such as tweezers, scissors, suturing needles, and the like may be disposed at the distal end of the housing such that they are functionally connected to the driveshaft. Means for controlling the instruments, typically opposed handles such as those found on household shears, are disposed at the proximal end of the housing such that they too are functionally connected to the driveshaft. The distally disposed instruments are operated by the surgeon by manipulation of the handles to impart an axial or rotary motion to the driveshaft and, in turn, the instrument.

In order to provide the surgeon with an instrument that enables precise and steady use, it is sometimes desirable that a complete operational cycle be possible using only one cycle of the device handle. Indeed, medical device engineers have long sought to enable a surgeon to impart phases of rotary and counter-rotary motion to the driveshaft in one continuous operation of the handles. However, it has not been possible previously to provide rapid rotational and immediate counter-rotational movement to a driveshaft during the same stroke.

Until now, the surgeon was required to complete one operation (i.e., opening or separating the handles) in order to provide rotary motion to the driveshaft and then a second operation (i.e., closing or drawing together the handles) in order to provide counter-rotary motion to the driveshaft. This inability to impart both rotary and counter-rotary motion to the driveshaft in one continuous operation of the handles results in devices that are limited in their applications and often awkward to use.

SUMMARY OF THE INVENTION

Accordingly, it is an object of the present invention to provide a handle and drive mechanism for providing a reciprocating rotary motion to a driveshaft first in one rotational direction and then immediately in the counter-rotational direction, with one or more additional rotation cycles possible.

It is a further object of the present invention to provide a mechanism capable of allowing a complete operational cycle using only one stroke of the device handle.

It is an additional object of the present invention to provide a mechanism for providing reciprocating rotary motion, wherein one or more changes in rotational direction may be controlled by manual manipulation of the device.

It is another object of the present invention to provide both rotational and counter-rotational motions to a fixed angular degree.

It is yet another object of the present invention to provide a medical device capable of accommodating a variety of effector distal end instruments that require such reciprocating rotational motion to operate.

A still further object of the present invention to provide an instrument of this type that is relatively easy to operate using only one hand.

The present invention comprises a hand-operated medical device that imparts, in one continuous operation of a handle mechanism, rotary motion to a driveshaft, first in one direction and then immediately in the opposite direction. Both rotation and counter-rotation motions are performed to a fixed angular degree. The purpose of providing these rotational motions to the driveshaft is to enable operation of various mechanisms that may be disposed at the distal end of the instrument. A handle of the present invention could be used to manipulate various distal end mechanisms, such as the suturing instrument described in U.S. Pat. No. 5,437,681 to Meade et al.

The above-described and other objects, features, and advantages of the present invention will become more apparent from the following detailed description of the preferred embodiments and certain modifications thereof when taken together with the accompanying drawings in which:

DETAILED DESCRIPTION

Figure 1A:
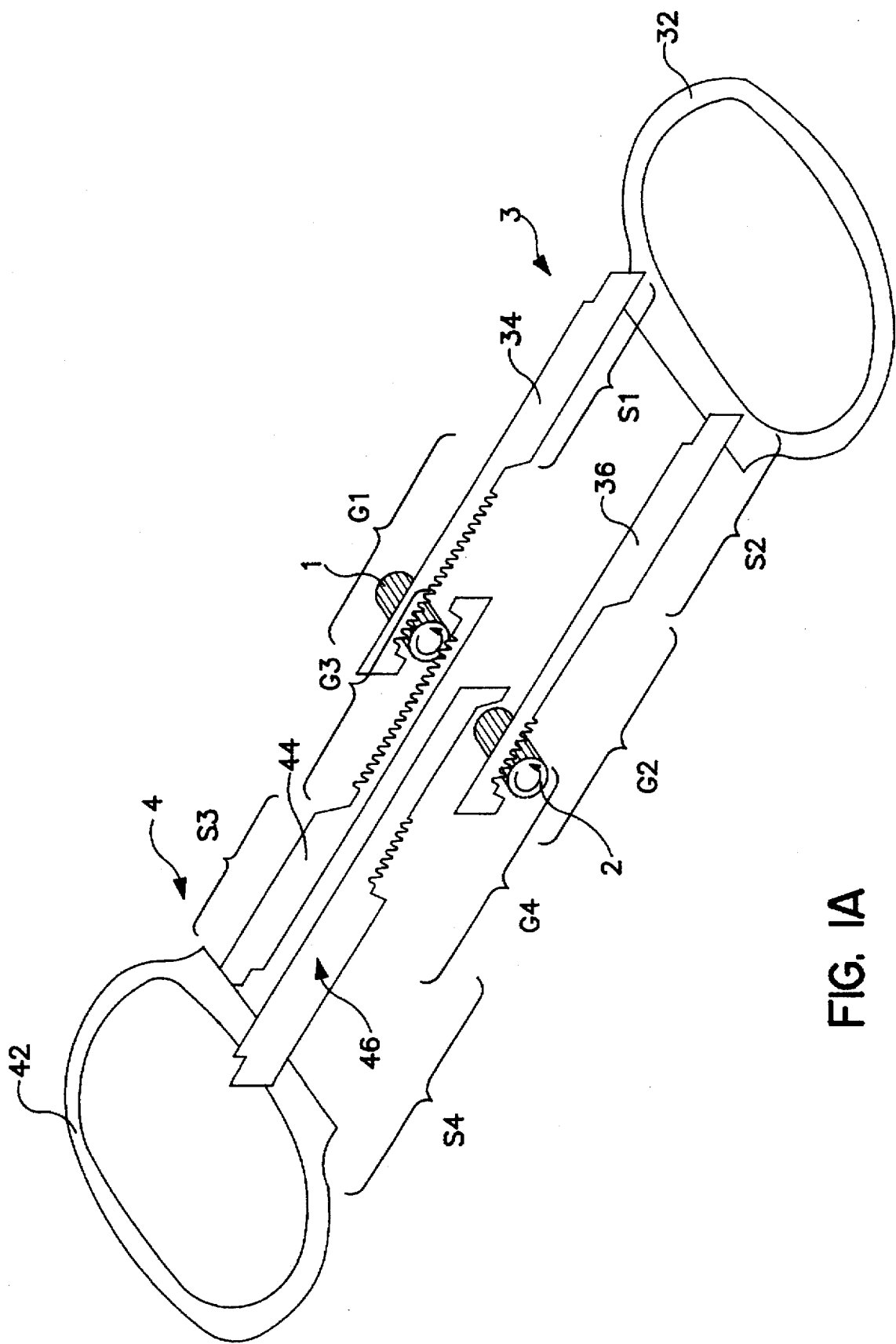
FIG. 1A is a perspective view of an embodiment of the present invention at the beginning of an operational stroke.

FIG. 1 shows an embodiment of the presently claimed invention. The invention comprises a first gear 1, a second gear 2, a first driving element 3, and a second driving element 4, both first driving element 3 and second driving element 4 being functionally and opposably connected to each of first gear 1 and second gear 2.

First driving element 3 has a first finger loop 32, preferably designed to accommodate a thumb, attached to two gear racks 34 and 36. Second driving element 4 has a second finger loop 42, preferably designed to accommodate an opposed finger of the same hand, most preferably the middle finger, attached to two gear racks 44 and 46.

Each of gear racks 34, 36, 44, and 46 comprise a support segment S1, S2, S3, and S4, respectively, and a recessed gear engagement segment G1, G2, G3, and G4, respectively. Gear rack 34 is identical in construction to gear rack 44 and respective recessed gear engagement segments G1 and G3 thereof are provided throughout their length with teeth that engage gear 1. However, as shown in FIGS. 1A–1C and FIG. 3, gear racks 34 and 44 disposed such that their toothed recessed gear engagement segments G1 and G3, respectively, opposably, simultaneously and continuously engage opposite sides of gear 1. This arrangement enables the smooth, continuous, synchronous operation of first driving element 3 and second driving element 4 throughout a manipulative stroke in which first finger loop 32 and second finger loop 42 are initially biased toward each other until they reach the innermost end of their travel length and, immediately thereafter, biased away from each other until they reach the outermost end of their travel length.

Figure 1B:
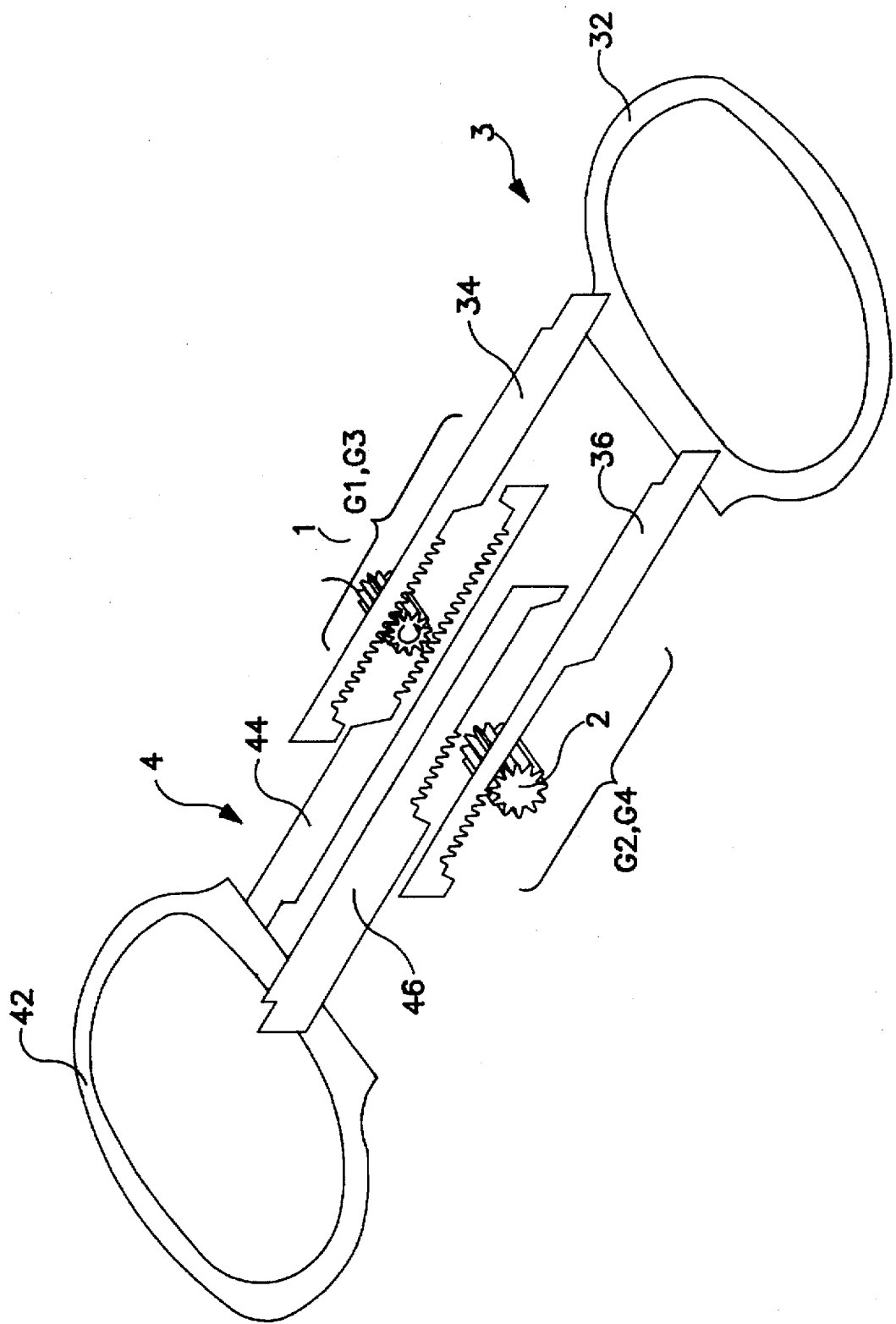
FIG. 1B is a perspective view of an embodiment of the present invention midway through an operational stroke.
Figure 1C:
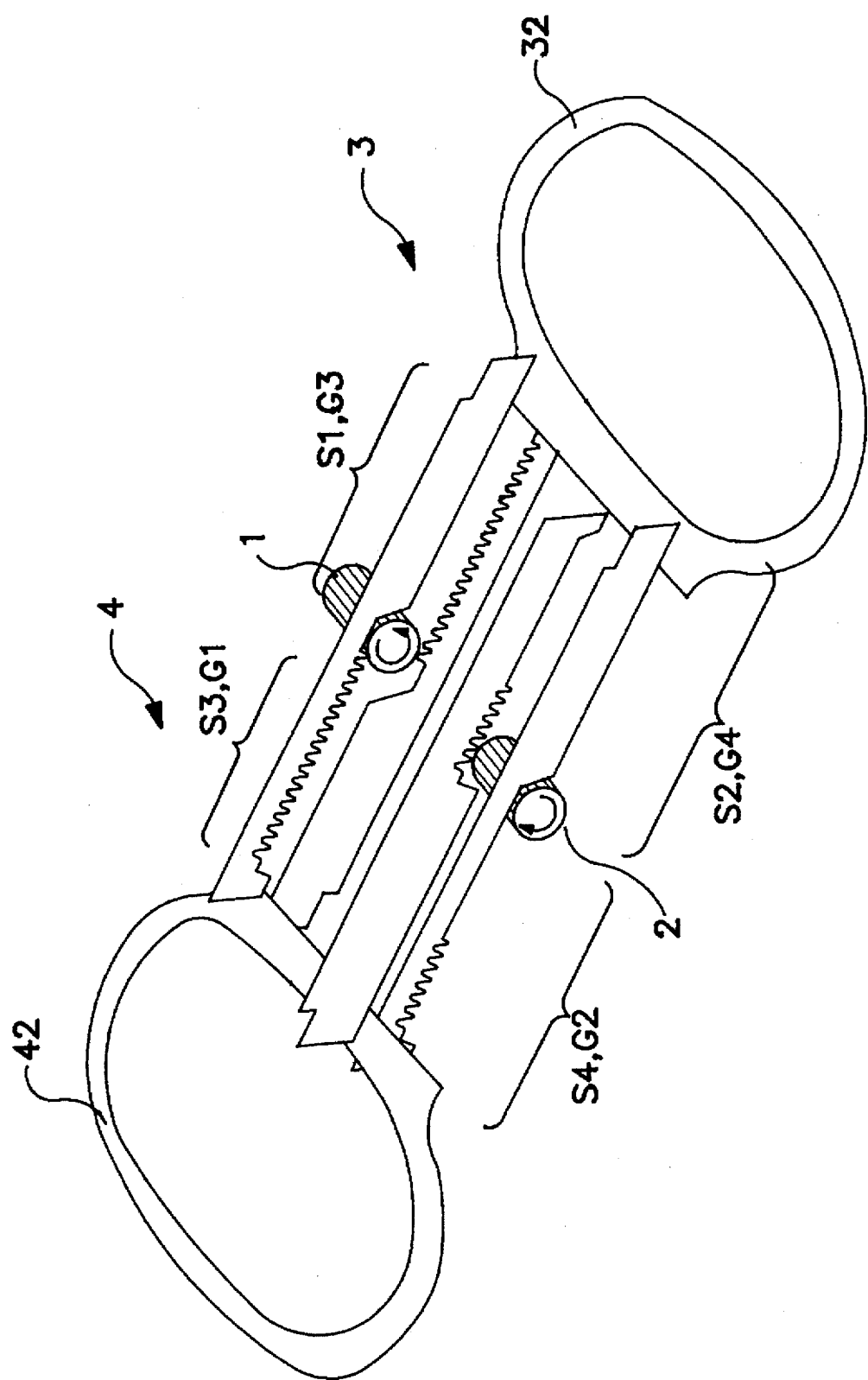
FIG. 1C is a perspective view of an embodiment of the present invention at the end of an operational stroke.

As further shown in FIGS. 1A–1C and FIG. 2, although gear rack 36 is similar in construction to gear rack 46, their respective recessed gear engagement segments G2 and G4 thereof are provided through different portions of their length with teeth that engage gear 1, such that the teeth of either segment G2 of gear rack 36 or segment G4 of gear rack 46, but not both simultaneously, engage gear 2. In this manner, gear 2 can be driven first in a rotary direction by gear rack 36, as shown in FIG. 1A, and then in a counter-rotary direction by gear rack 46, as shown in FIG. 1B, or vice versa, depending on the arrangement of segments G2 and G4, as first driving element 3 and second driving element 4 are biased toward each other.

Thus, as first driving element 3 and second driving element 4 are moved through a complete cycle by manipulation of first finger loop 32 and second finger loop 42, gear 2 will experience four distinct phases of alternating rotary and counter-rotary motion. The frequency and duration of each pair of phases depends solely upon the arrangement of teeth in segments G2 and G4. E.g., six distinct phases of alternating rotary and counter-rotary motion would result if either of segments G2 or G4 were provided with teeth at the outermost portions of their length and the other segment provided with teeth intermediate between those of its opposite member and eight distinct phases of alternating rotary and counter-rotary motion would result if segments G2 and G4 were each provided with teeth through two, staggered, portions of their length.

Figure 2:
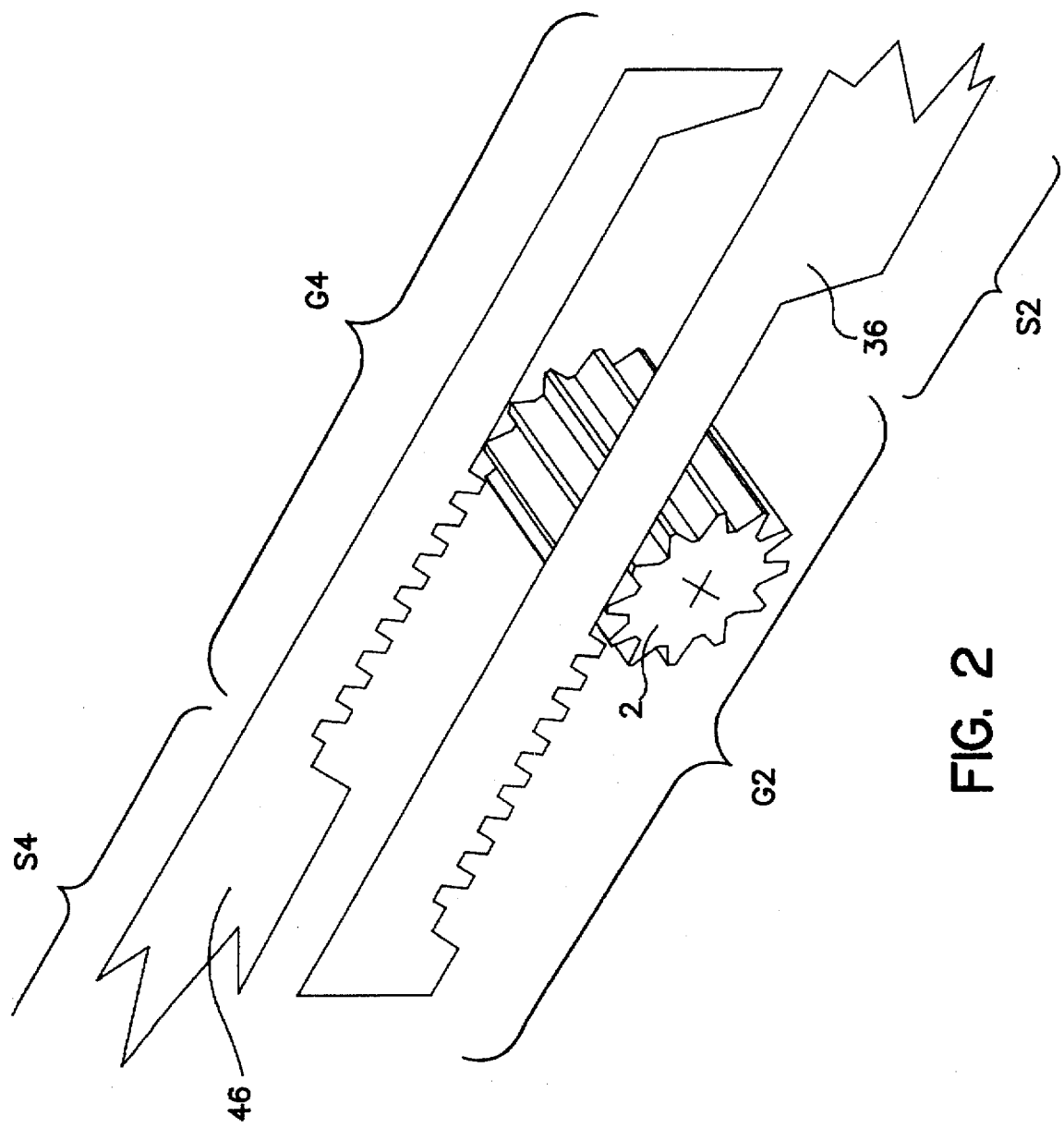
FIG. 2 is a close-up perspective view of an embodiment of the reciprocating gear assembly of the present invention at a changeover point.
Figure 3A:
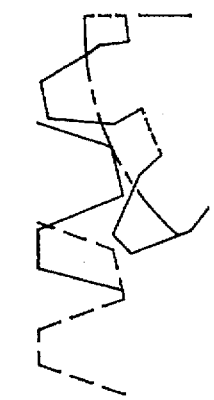
FIG. 3 is a segmented elevation of the gearing cogs on the gears and gear racks of the present invention.
Figure 3B:
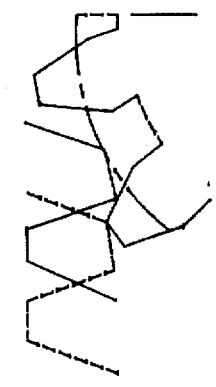
Figure 3C:
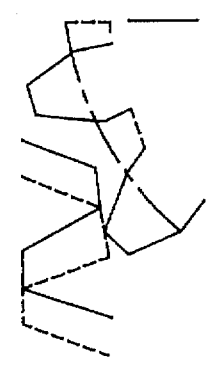
Figure 3D:
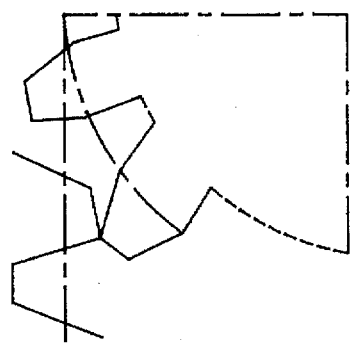

FIGS. 1B and 2 show first driving element 3 and second driving element 4 at their mid-position; this is the changeover point for engagement of gear racks 36 and 46. Further motion of first driving element 3 and second driving element 4 in either direction will cause engagement of one rack and disengagement of the other. As shown in FIG. 3, each cog tooth on gear 1 and gear 2 is beveled in cross-section, enabling identical engagement with gear racks 36 and 46 regardless of the direction of engagement, thereby resulting in identical rotary motion of gear 2 in both the rotary and counter-rotary directions. With respect to gear racks 36 and 46, this feature enables precise and stable reciprocating rotary motion of a driveshaft without "catches" or discontinuities of motion by providing a smooth changeover of engagement from the teeth of one rack to those of the other, and, as a result, the smooth transition between rotary and counter-rotary motion of gear 2.

An additional benefit of this arrangement of teeth is that a surgeon can control the duration of motion in either or both the rotary and counter-rotary directions, up to a maximum determined by the length of segments G2 and G4 about the changeover point that are toothed. This is accomplished by positioning first driving element 3 and second driving element 4 such that the teeth of gear racks 36 and 46 are at a changeover point. Next, the surgeon can bias driving elements 3 and 4 toward or away from each other, depending on whether rotary or counter-rotary motion is desired.

Figure 4:
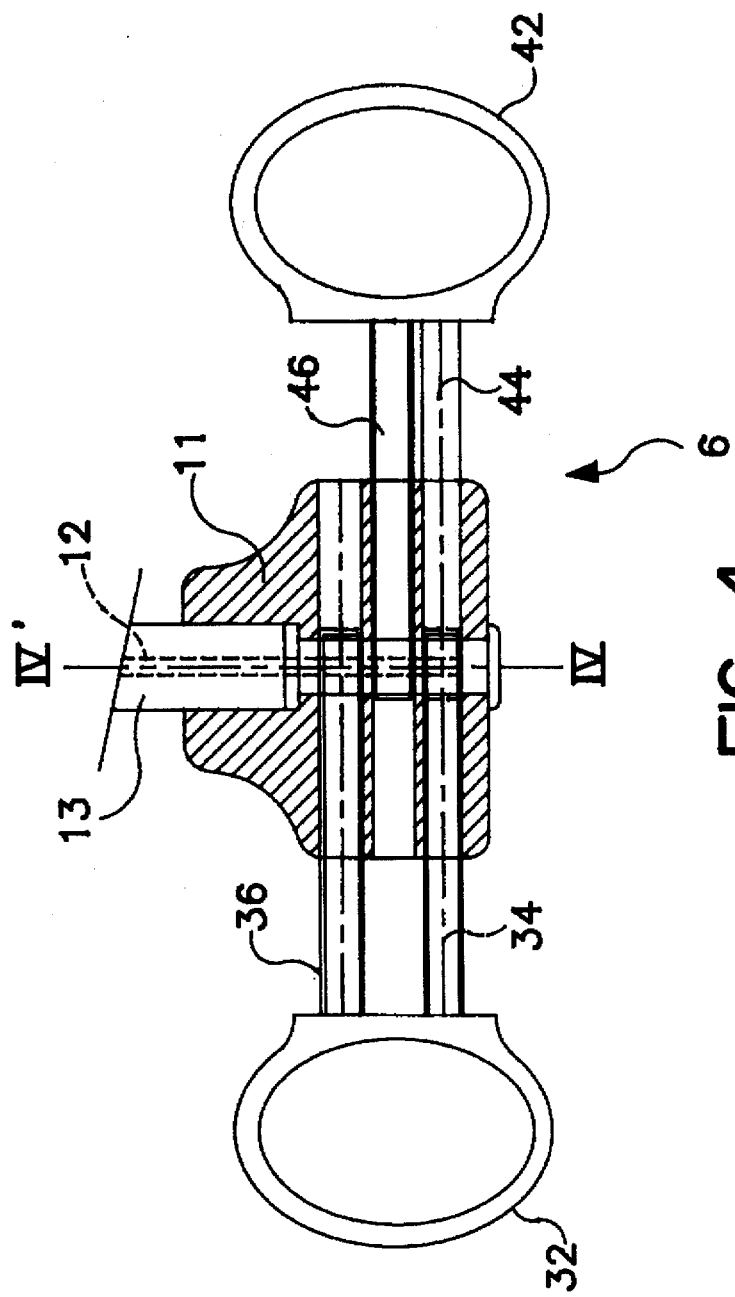
FIG. 4 is a plan view of the apparatus of the present invention.
Figure 5:
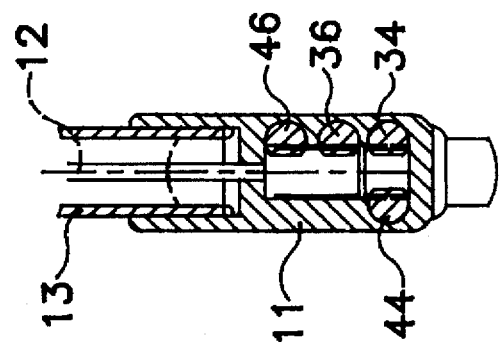
FIG. 5 is a side elevation view of the handle and driveshaft shown in FIG. 4 taken through the line IV—IV'.

FIG. 4 views the instrument handle 6 in cross section with the main body 11, distal shaft 12, and distal outer tube 13 in combination with first gear 1, second gear 2, first driving element 3, and second driving element 4. FIG. 5 shows a side elevation cross-section view of the handle and driveshaft of FIG. 4 taken through the line IV—IV'. As can be seen from FIGS. 1A–1C, 2, and 5, gear racks 36 and 46 may be oriented so that they engage gear 2 in a side-by-side fashion, although it is envisioned that they may be opposably disposed, as are gear racks 34 and 44.

To reiterate the cycle sequence, starting with first driving element 3 and second driving element 4 in the position furthest apart from each other and cycling the instrument once, i.e., biasing them completely toward each other and then back to the original position, the driveshaft rotates in a first, rotary direction. One quarter of the way through the cycle, the driveshaft reverses direction and rotate in a second, counter-rotary direction. As the first and second driving elements are biased to the fully together position, the halfway point of the cycle is reached. As the driving elements are biased apart, the driveshaft again reverses direction rotates in the first, rotary direction. At the three-quarters point of the cycle, the driveshaft again reverses direction and completes the cycle moving in the second, counter-rotary direction.

In an additional contemplated embodiment, it is intended that the device housing be provided with one fixed finger loop and one driving element such that the reciprocating rotary motion of the driveshaft is accomplished solely by means of manipulating the single drive element.

It can now be understood that the starting rotational direction and the number and durations of gear motion phases of the mechanism can be established when manufacturing the instrument by varying the number and placement of gear teeth on gear racks 36 and 46. It may also be understood that the degree of angular rotation of gear 2 is controlled by the length of gear racks 36 and 46 and the pitch diameter of driving gear 2.

What is claimed is:

1. Apparatus to effect reciprocating rotation of a driveshaft comprising:
   (a) a first set of two gear racks comprising
      (i) a first gear rack including a toothed portion over a first length, and
      (ii) a second gear rack fixed in a position parallel to said first gear rack, including a toothed portion over a second length,
   (b) a first gear engaging said first gear rack of said first set of gear racks,
   (c) a second gear attached to said driveshaft, said second gear engaging said second gear rack of said first set of gear racks,
   (d) a second set of two gear racks movable reciprocally relative to said first set of gear racks and comprising
      (i) a first gear rack including a toothed portion over a third length substantially identical to the toothed portion over said first length of said first gear rack of said first set of gear racks and engaging said first gear rack on a side of said first gear opposite the side on which said first gear rack of said first set of gear racks engages said first gear, and
      (ii) a second gear rack fixed in a position parallel to said first gear rack of said second set of gear racks, having a toothed portion over a fourth length oriented to engage along said fourth length said second gear rack on the same side of said second gear as said second gear rack of said first set of gear racks engages along said second length said second gear such that when said first set of gear racks is moved in a single direction relative to said second set of gear racks, engagement of over said second length produces a first rotational motion of said second gear and engagement over said fourth length produces an opposite rotational motion of said second gear.

2. Apparatus to effect reciprocating rotation of a driveshaft comprising:

(a) a gear attached to said driveshaft;

(b) a first gear rack including a toothed portion over a first length, said first gear rack disposed such that said toothed portion over a first length is capable of engaging said gear;

(c) a second gear rack movable reciprocally relative to said first gear rack and including a toothed portion over a second length, said second gear rack disposed such that said toothed portion over a second length is capable of engaging said gear;

wherein when said first gear rack is moved in a single direction relative to said second gear rack, engagement of said toothed portion over said first length produces a first rotational motion of said gear and engagement of said toothed portion over said second length produces an opposite rotational motion of said gear.

3. Handheld apparatus to effect reciprocating rotation of a driveshaft comprising:

(a) a first gear attached to said apparatus such that said first gear is capable of independent reciprocating rotary motion, (b) a second gear attached to said driveshaft in combination such that said combination is capable of reciprocating rotary motion, (c) a first driving element having a first finger loop and comprising a stabilizing gear rack having teeth provided throughout its length and a driving gear rack having teeth provided throughout one or more portions of its length, and (d) a second, opposed driving element having a second finger loop and also comprising a stabilizing gear rack having teeth provided throughout its length and a driving gear rack having teeth provided throughout one or more portions of its length such that said second driving element driving gear rack teeth alternate in their position along the length of said second driving element driving gear rack relative to those of said first driving element driving gear rack, wherein both of said stabilizing gear racks of said first driving element and said second driving element are opposably disposed such that they continuously engage said first gear, and wherein both of said driving gear racks of said first driving element and said second driving element are laterally disposed such that they alternate in their engagement of said second gear.

4. Apparatus, as claimed in claim 3, wherein one of said finger loops is preferably designed to accommodate a thumb.

5. Apparatus, as claimed in claim 4, wherein the second of said finger loops is preferably designed to accommodate an opposed finger of the same hand of said thumb.

6. Apparatus, as claimed in claim 3, wherein the arrangement of teeth on said driving gear racks of said first driving element and said second driving element enable four distinct phases of rotary and counter-rotary motion.

7. Apparatus, as claimed in claim 3, wherein the arrangement of teeth on said driving gear racks of said first driving element and said second driving element enable six distinct phases of rotary and counter-rotary motion during a single complete operational cycle.

8. Apparatus, as claimed in claim 3, wherein the arrangement of teeth on said driving gear racks of said first driving element and said second driving element enable eight distinct phases of rotary and counter-rotary motion.

9. Apparatus, as claimed in claim 3, wherein said teeth of said first and said second gears are beveled in cross-section, enabling identical engagement with said gear racks of said first and said second driving elements regardless of the direction of engagement, thereby resulting in identical rotary motion of gear 2 in both the rotary and counter-rotary directions.

10. Apparatus, as claimed in claim 3, wherein the apparatus is capable of providing precise and stable reciprocating rotary motion of said driveshaft by providing a smooth changeover of engagement from the teeth of one rack to those of the other, and, as a result, the smooth transition between rotary and counter-rotary motion of said second gear.

11. Apparatus, as claimed in claim 3, wherein the apparatus is capable of enabling an operator to control the duration of the driveshaft motion in either or both the rotary and counter-rotary directions, up to a maximum duration determined by the length of the said first and second driving gear racks that are toothed about the changeover.

12. Apparatus, as claimed in claim 3, wherein the tension of the driving elements is determined by means of the gearing ratio between said gears.

13. Apparatus to effect reciprocating rotation of a driveshaft in a handheld instrument comprising:

(a) a first gearing means attached to said apparatus such that said first gearing means is capable of independent reciprocating rotary motion, (b) a second gearing means attached to said driveshaft such that said combination is capable of reciprocating rotary motion, (c) a first driving means capable of driving said first and second gearing means, and (d) a second, opposed driving means also capable of driving said first and second gearing means wherein both of said first and second driving means are capable of continuously engaging said first gearing means, and wherein both of said first and second driving means are capable of alternately engaging said second gearing means.

* * * * *